(12) United States Patent
Beier et al.

(10) Patent No.: US 8,361,526 B2
(45) Date of Patent: Jan. 29, 2013

(54) METHOD OF PREPARING A DOUGH-BASED PRODUCT

(75) Inventors: Lars Beier, Lyngby (DK); Esben Peter Friis, Herlev (DK); Henrik Lundqvist, Malmo (SE); Peter Kamp Hansen, Lejre (DK); Tina Spendler, Maaloev (DK)

(73) Assignee: Novozymes A/S, Bagsvaerd (DK)

( * ) Notice: Subject to any disclaimer, the term of this patent is extended or adjusted under 35 U.S.C. 154(b) by 407 days.

(21) Appl. No.: 12/602,570

(22) PCT Filed: Jun. 5, 2008

(86) PCT No.: PCT/EP2008/056999
§ 371 (c)(1),
(2), (4) Date: May 11, 2010

(87) PCT Pub. No.: WO2008/148845
PCT Pub. Date: Dec. 11, 2008

(65) Prior Publication Data
US 2010/0215802 A1    Aug. 26, 2010

Related U.S. Application Data

(60) Provisional application No. 60/944,543, filed on Jun. 18, 2007.

(30) Foreign Application Priority Data

Jun. 7, 2007   (EP) ..................................... 07109793

(51) Int. Cl.
*A21D 8/04*  (2006.01)
*C12N 9/28*  (2006.01)

(52) U.S. Cl. ......................................... 426/28; 435/202

(58) Field of Classification Search ....................... None
See application file for complete search history.

(56) References Cited

U.S. PATENT DOCUMENTS 3,026,205 A    3/1962   Stone et al.
6,162,628 A   12/2000   Cherry et al.

FOREIGN PATENT DOCUMENTS

WO    WO 91/04669      4/1991
WO    WO 2006/032281   3/2006

OTHER PUBLICATIONS

Beier et al, Hydrolase, p. 1-112 (1999).

*Primary Examiner* — Tekchand Saidha
*Assistant Examiner* — Md. Younus Meah
(74) *Attorney, Agent, or Firm* — Kristin J. McNamara

(57) ABSTRACT

Dough with a high sucrose content (such as cake dough) tends to inhibit the activity of an anti-staling amylase such as Novamyl®, making it less effective to prevent the staling of dough-based products with high sucrose content such as cakes. A good anti-staling effect in cakes can be achieved by using a carefully selected anti-staling amylase with certain properties. Analysis of a 3D structure of Novamyl® shows that sucrose may inhibit by binding in the active site. Sucrose docks into the active site of Novamyl® differently from the substrate or inhibitor in published models 1QHO and 1QHP. This finding is used to design sucrose-tolerant variants.

20 Claims, 1 Drawing Sheet

```
ATOM      1  C1   GLC A   1      39.217  71.096  23.310  1.00 53.03           C
ATOM      2  C2   GLC A   1      38.281  69.893  23.579  1.00 55.06           C
ATOM      3  O2   GLC A   1      37.370  70.251  24.614  1.00 58.15           O
ATOM      4  C3   GLC A   1      39.115  68.665  24.014  1.00 52.01           C
ATOM      5  O3   GLC A   1      38.239  67.559  24.250  1.00 51.59           O
ATOM      6  C4   GLC A   1      40.134  68.335  22.918  1.00 53.38           C
ATOM      7  O4   GLC A   1      41.075  67.354  23.379  1.00 56.10           O
ATOM      8  C5   GLC A   1      40.910  69.552  22.419  1.00 55.06           C
ATOM      9  O5   GLC A   1      40.130  70.771  22.258  1.00 55.28           O
ATOM     10  C6   GLC A   1      41.528  69.246  21.045  1.00 52.65           C
ATOM     11  O6   GLC A   1      42.190  70.422  20.599  1.00 38.28           O
ATOM     12  H01  GLC A   1      41.470  68.299  20.510  1.00 52.65           H
ATOM     13  H02  GLC A   1      38.649  71.976  23.008  1.00 53.03           H
ATOM     14  H03  GLC A   1      37.734  69.638  22.672  1.00 55.06           H
ATOM     15  H04  GLC A   1      37.860  70.513  25.396  1.00 58.15           H
ATOM     16  H05  GLC A   1      39.655  68.880  24.937  1.00 52.01           H
ATOM     17  H06  GLC A   1      37.543  67.825  24.856  1.00 51.59           H
ATOM     18  H07  GLC A   1      41.666  67.115  22.661  1.00 56.10           H
ATOM     19  C1   FRU A   2      39.472  73.740  24.328  1.00 56.70           C
ATOM     20  O1   FRU A   2      39.013  73.640  22.974  1.00 60.98           O
ATOM     21  C2   FRU A   2      40.511  72.650  24.697  1.00 60.03           C
ATOM     22  O2   FRU A   2      39.917  71.335  24.487  1.00 54.05           O
ATOM     23  C3   FRU A   2      41.038  72.717  26.169  1.00 56.66           C
ATOM     24  O3   FRU A   2      40.143  72.012  27.049  1.00 57.01           O
ATOM     25  C4   FRU A   2      42.371  71.945  26.006  1.00 56.00           C
ATOM     26  O4   FRU A   2      43.252  72.139  27.103  1.00 53.30           O
ATOM     27  C5   FRU A   2      42.866  72.599  24.701  1.00 54.87           C
ATOM     28  O5   FRU A   2      41.705  72.741  23.843  1.00 54.62           O
ATOM     29  C6   FRU A   2      43.903  71.816  23.946  1.00 55.79           C
ATOM     30  O6   FRU A   2      44.464  72.647  22.938  1.00 54.56           O
ATOM     31  H01  FRU A   2      43.759  73.046  22.423  1.00 54.56           H
ATOM     32  H02  FRU A   2      38.615  73.643  24.994  1.00 56.70           H
ATOM     33  H03  FRU A   2      38.363  74.325  22.804  1.00 60.98           H
ATOM     34  H04  FRU A   2      41.133  73.718  26.592  1.00 56.66           H
ATOM     35  H05  FRU A   2      40.267  71.066  26.941  1.00 57.01           H
ATOM     36  H06  FRU A   2      42.287  70.859  25.973  1.00 56.00           H
ATOM     37  H07  FRU A   2      42.807  71.896  27.918  1.00 53.30           H
ATOM     38  H08  FRU A   2      43.345  73.538  24.976  1.00 54.87           H
ATOM     39  H09  FRU A   2      43.440  70.944  23.487  1.00 55.79           H
ATOM     40  H10  FRU A   2      44.686  71.486  24.630  1.00 55.79           H
ATOM     41  H11  FRU A   2      39.962  74.708  24.436  1.00 56.70           H
```

METHOD OF PREPARING A DOUGH-BASED PRODUCT

CROSS-REFERENCE TO RELATED APPLICATIONS

This application is a 35 U.S.C. 371 national application of PCT/EP2008/056999 filed Jun. 5, 2008, which claims priority or the benefit under 35 U.S.C. 119 of European application no. 07109793.5 filed Jun. 7, 2007 and U.S. provisional application No. 60/944,543 filed Jun. 18, 2007, the contents of which are fully incorporated herein by reference.

SEQUENCE LISTING

The present invention comprises a sequence listing.

DEPOSIT OF BIOLOGICAL MATERIAL

None.

FIELD OF THE INVENTION

The present invention relates to the use of anti-staling amylases in the preparation of dough or dough-based edible products with a high sucrose content.

BACKGROUND OF THE INVENTION

U.S. Pat. No. 3,026,205 describes a process of producing baked confections and the products resulting therefrom by alpha-amylase.

WO 9104669 describes the use of a maltogenic alpha-amylase to retard the staling of baked products such as bread; the maltogenic alpha-amylase described therein is commercially available under the tradename Novamyl® (product of Novozymes A/S). U.S. Pat. No. 6,162,628 describes Novamyl® variants and their use for the same purpose. Three-dimensional structures of Novamyl® are published in U.S. Pat. No. 6,162,628 and in the Protein Data Bank (available at http://www.rcsb.org/pdb/) with identifiers 1QHO and 1QHP, the structures are included herein by reference.

WO 2006/032281 describes methods of preparing a dough-based product with a high sucrose content using anti-staling amylases.

SUMMARY OF THE INVENTION

The inventors have found that a high sucrose content dough (such as cake dough) tends to inhibit the activity of an anti-staling amylases such as Novamyl®, making it less effective to prevent the staling of dough-based products with high sucrose content such as cakes. They have found that a good anti-staling effect in cakes can be achieved by using a carefully selected anti-staling amylase with certain properties, and they have identified such amylases.

By analyzing a 3D structure of Novamyl®, the inventors further found that sucrose may inhibit by binding in the active site. They have found that sucrose docks into the active site of Novamyl® differently from the substrate or inhibitor in published models 1QHO and 1QHP, and they have used this finding to design sucrose-tolerant variants. A selection of particularly interesting Novamyl® (SEQ ID NO:1) variants were identified comprising the two specific substitutions D261G and T288P in combination with at least one other amino acid alteration, preferably at least two other amino acid alterations, or three other amino acid alterations, or most preferably in combination with at least four other amino acid alterations.

Accordingly, in a first aspect the invention provides a method of preparing a dough or a dough-based edible product, comprising adding a polypeptide to the dough, wherein the dough comprises at least 10% sucrose by weight, and the polypeptide has an amino acid sequence which is at least 70% identical to SEQ ID NO: 1, and compared to SEQ ID NO: 1 comprises the two substitutions D261G and T288P and at least one additional amino acid alteration which is substitution or deletion of or insertion adjacent to Y89, W93, P191, F194, Y360, or N375.

In a second aspect, the invention provides polypeptides, which have amylase activity less inhibited by sucrose than the amylase activity of SEQ ID NO: 1, which have an amino acid sequence which is at least 70% identical to SEQ ID NO: 1, and which when compared to SEQ ID NO: 1 comprises the two substitutions D261G and T288P and at least one additional amino acid alteration, which is substitution or deletion of or insertion adjacent to Y89, W93, P191, F194, Y360, or N375. The invention also provides methods of producing such novel sucrose tolerant polypeptide variants of a maltogenic alpha-amylase.

BRIEF DESCRIPTION OF DRAWINGS

Docking of sucrose into the active site of Novamyl® (using the software GOLD version 2.1.2, Cambridge Crystallographic Data Centre, 12 Union Road, Cambridge, CB2 1EZ, UK and the protein part of the x-ray structure 1QHO.pdb) reveals a specific binding configuration as unique to sucrose. The cartesian coordinates for the sucrose atoms in this binding configuration, using the coordinate system of the x-ray structure 1QHO.pdb are given in FIG. 1.

DETAILED DESCRIPTION OF THE INVENTION

Maltogenic Alpha-Amylase and Sucrose Docking

A maltogenic alpha-amylase (EC 3.2.1.133) having more than 70% identity, such as, at least 75%, (particularly more than 80% identity, such as at least 85%, or 90% identity, such as at least 95% or 96% or 97% or 98% or 99%) with the Novamyl® sequence shown as SEQ ID NO: 1 may be used as the parent enzyme for designing sucrose tolerant variants. Amino acid identity may be calculated as described in U.S. Pat. No. 6,162,628.

For Novamyl® (SEQ ID NO: 1), a 3D structure including a substrate or inhibitor as described in U.S. Pat. No. 6,162,628 or in the Protein Data Bank with the identifier 1QHO or 1QHP may be used. Alternatively, a Novamyl® variant may be used, such as a variant described in U.S. Pat. No. 6,162,628 or in this specification, e.g. the variant F188L+D261G+T288P, which is used as a reference enzyme in the examples below. A 3D structure of a variant may be developed from the Novamyl® structure by known methods, e.g. as described in T. L. Blundell et al., Nature, vol. 326, p. 347 if (26 Mar. 1987); J. Greer, Proteins: Structure, Function and Genetics, 7:317-334 (1990); or Example 1 of WO 9623874.

The inventors found that sucrose may inhibit Novamyl® by binding in the active site. Docking of sucrose into the active site of Novamyl® (using the software GOLD version 2.1.2, Cambridge Crystallographic Data Centre, 12 Union Road, Cambridge, CB2 1EZ, UK and the protein part of the x-ray structure 1 QHO.pdb) reveals a specific binding configuration as unique to sucrose. The cartesian coordinates for the sucrose atoms in this binding configuration, using the coordinate system of the x-ray structure 1QHO.pdb are given in FIG. 1.

Maltogenic Alpha-Amylase Assay

The activity of a maltogenic alpha-amylase may be determined using an activity assay such as the MANU method. One MANU (Maltogenic Amylase Novo Unit) is defined as the amount of enzyme required to release one micro-mole of maltose per minute at a concentration of 10 mg of maltotriose substrate per ml in 0.1 M citrate buffer at pH 5.0, 37° C. for 30 minutes.

Amino Acid Alterations

The amino acid sequence of a maltogenic alpha-amylase may be altered to decrease the sucrose inhibition. The inventors found that the alteration may be made at an amino acid residue having at least one atom within 4 Angstroms from any of the sucrose atoms when the sucrose molecule is docked in the 3D structure of the maltogenic alpha-amylase. Using the Novamyl® structure 1QHO and the sucrose docking in FIG. 1, the following residues are within 4 Å: K44, N86, Y89, H90, Y92, W93, F188, T189, D190, P191, A192, F194, D372, P373, R376.

Further the following two positions of SEQ ID NO: 1 have been identified as relevant: Y360 and N375.

Particularly preferred embodiments of the invention are amino acid alterations in the following 2-6 positions compared to Novamyl® (SEQ ID NO: 1) in combination with the two specific substitutions D261G and T288P:

Y89+W93
Y89+P191
Y89+F194
Y89+Y360
Y89+N375
W93+P191
W93+F194
W93+Y360
W93+N375
P191+F194
P191+Y360
P191+N375
F194+Y360
F194+N375
Y360+N375
Y89+W93+P191
Y89+W93+F194
Y89+W93+Y360
Y89+W93+N375
Y89+P191+F194
Y89+P191+Y360
Y89+P191+N375
Y89+F194+Y360
Y89+F194+N375
Y89+Y360+N375
W93+P191+F194
W93+P191+Y360
W93+P191+N375
W93+F194+Y360
W93+F194+N375
W93+Y360+N375
P191+F194+Y360
P191+F194+N375
P191+Y360+N375
F194+Y360+N375
Y89+W93+P191+F194
Y89+W93+P191+Y360
Y89+W93+P191+N375
Y89+W93+F194+Y360
Y89+W93+F194+N375
Y89+W93+Y360+N375
Y89+P191+F194+Y360
Y89+P191+F194+N375
Y89+P191+Y360+N375
Y89+F194+Y360+N375
W93+P191+F194+Y360
W93+P191+F194+N375
W93+P191+Y360+N375
W93+F194+Y360+N375
P191+F194+Y360+N375
Y89+W93+P191+F194+Y360
Y89+W93+P191+F194+N375
Y89+W93+P191+Y360+N375
Y89+W93+F194+Y360+N375
Y89+P191+F194+Y360+N375
W93+P191+F194+Y360+N375
Y89+W93+P191+F194+Y360+N375

The alteration may be a substitution or deletion of one or more of the selected residues, or one or more residues (particularly 1-4 residues or 5-6 residues) can be inserted adjacent to a selected residue.

The substitution may be with a smaller or larger residue. A substitution to increase the size of the residue may diminish the space obtained by the docked sucrose molecule thereby preventing the binding of sucrose. Amino acid residues are ranked as follows from smallest to largest: (an equal sign indicates residues with sizes that are practically indistinguishable):

G<A=S=C<V=T<P<L=I=N=D=M<E=Q<K<H<R< F≦Y≦W

The substitution may also be such as to eliminate contacts with the sucrose molecule, in particular by moving or removing potential sites of hydrogen bonding or Van der Waals interactions.

The substitution may particularly be with another residue of the same type where the type is negative, positive, hydrophobic or hydrophilic. The negative residues are D, E, the positive residues are K/R, the hydrophobic residues are A, C, F, G, I, L, M, P, V, W, Y, and the hydrophilic residues are H, N, Q, S, T.

Some particular examples of substitutions are I15T/S/V/L, R18K, K44R/S/T/Q/N, N86Q/S/T, T87N/Q/S, G88A/S/T, Y89W/F/H, H90W/F/Y/R/K/N/Q/M, W93Y/F/M/E/G/N/T/S, F188H/L/I/T/G/V, D190E/Q/G, P191S/N, A192S/T, F194S/L/Y, L196F, Y360F/I/N, N371K/R/F/Y/Q, D372E/Q/S/T/A and N375S/T/D/E/Q.

Most preferred embodiments of amino acid alterations in the above-listed preferred positions are the following substitutions, alone or in combination:

Y89F, W
W93F, Y
P191S, N
F194Y, S, L
Y360F, I, N
N375S, T

Examples of deletions are deletion of residue 191 or 192. An example of an insertion is Ala inserted between 192 and 193.

The polypeptide may include other alterations compared to Novamyl® (SEQ ID NO: 1), e.g. alterations to increase the thermostability as described in U.S. Pat. No. 6,162,628.

Particularly preferred embodiments of the invention are the following amino acid alterations compared to Novamyl® (SEQ ID NO: 1), all of which are tested in the examples below:

Y89F, D261G, T288P, I290V, N375S
F194Y, D261G, T288P, N375S

I15T, P191S, D261G, T288P, N375S, S640I
Y89F, P191S, D261G, T288P
I15T, Y89F, P191S, D261G, T288P
Y89F, F194Y, D261G, T288P
Y89F, D261G, T288P, N375S
Y89F, P191S, F194Y, D261G, T288P
Y89F, P191S, D261G, T288P, N3755
Y89F, P191S, D261G, T288P, Y360N
Y89F, P191S, D261G, T288P, Y360F
Y89F, W93Y, P191S, D261G, T288P
Y89F, W93F, P191S, D261G, T288P
Y89F, P191S, F194Y, D261G, T288P, N3755

Nomenclature for Amino Acid Alterations

In this specification, an amino acid substitution is described by use of one-letter codes, e.g. K44R. Slashes are used to indicate alternatives, e.g. K44R/S/T/Q/N to indicate substitution of K44 with R or S etc. P191* indicates a deletion of P191. *192aA indicates insertion of one Ala after A192. Commas are used to indicate multiple alterations in the sequence, e.g. F188L, D261G, T288P to indicate a variant with three substitutions.

Properties of Anti-Staling Amylase for Use with Sucrose

The amylase for use in high-sucrose dough may be selected so as to have mainly exo-amylase activity. More specifically, the amylase hydrolyzes amylose so that the average molecular weight of the amylose after 0.4-4% hydrolysis is more than 50% (particularly more than 75%) of the molecular weight before the hydrolysis.

Thus, the amylase may hydrolyze amylose (e.g. wheat amylose or synthetic amylose) so that the average molecular weight of the amylose after 0.4-4% hydrolysis (i.e. between 0.4-4% hydrolysis of the total number of bonds) is more than 50% (particularly more than 75%) of the value before the hydrolysis. The hydrolysis can be conducted in a 1.7% amylose solution by weight at suitable conditions (e.g. 10 minutes at 60° C., pH 5.5), and the molecular weight distribution before and after the hydrolysis can be determined by HPLC. The test may be carried out as described in C. Christophersen et al., Starch 50 (1), 39-45 (1998).

An exo-amylase for use in high-sucrose dough may have a specified sugar tolerance. Compared to its activity in the absence of sucrose, the amylase may have more than 20° A activity at 10% sugar, more than 10% activity at 20% sucrose, or more than 4% activity at 40° A sucrose. The sugar tolerance may be determined as described in the examples.

The exo-amylase may have optimum activity in the pH range 4.5-8.5. It may have sufficient thermostability to retain at least 20% (particularly at least 40%) activity after 30 minutes incubation at 85° C. at pH 5.7 (50 mM Na-acetate, 1 mM CaCl$_2$) without substrate.

The exo-amylase may be added to the dough in an amount corresponding to 1-100 mg enzyme protein per kg of flour, particularly 5-50 mg per kg.

The exo-amylase may be non-liquefying. This can be determined by letting the exo-amylase act on a 1% wheat starch solution until the reaction is complete, i.e. addition of fresh enzyme causes no further degradation, and analyzing the reaction products, e.g. by HPLC. Typical reaction conditions are e.g. 0.01 mg enzyme per ml starch solution for 48 hours. The exo-amylase is considered non-liquefying if the amount of residual starch after the reaction is at least 20% of the initial amount of starch.

The exo-amylase may have maltogenic alpha-amylase activity (EC 3.2.1.133). The exo-amylase may be the amylase described in WO 2005/066338, or it may be a Novamyl® variant described in this specification.

Dough and Dough-Based Edible Product

The dough may have a sucrose content above 10% by weight, particularly above 20% or 30%, e.g. 30-40%. The flour content is typically 25-35% by weight of total ingredients. The dough may be made by a conventional cake recipe, typically with cake flour, sugar, fat/oil and eggs as the major ingredients. It may include other conventional ingredients such as emulsifiers, humectants, gums, starch and baking powder. It generally contains such ingredients as soft wheat flour, milk or other liquids, sugar, eggs, chemical leaveners, flavor extracts and spices, as well as others that may or may not include shortening.

Examples of emulsifiers include mono- or diglycerides, sugar esters of fatty acids, polyglycerol esters of fatty acids, lactic acid esters of monoglycerides, acetic acid esters of monoglycerides, polyoxethylene stearates, or lysolecithin. Conventional emulsifiers used in making flour dough products include as examples monoglycerides, diacetyl tartaric acid esters of mono- and diglycerides of fatty acids, and lecithins e.g. obtained from soya. The emulsifying agent may be an emulsifier per se or an agent that generates an emulsifier in situ. Examples of emulsifying agents that can generate an emulsifier in situ include enzymes, such as, lipase or phospholipases.

The dough is generally heat treated, e.g. by baking or deep frying to prepare an edible product such as cakes including pound cake, yellow and white layer cakes, cakes containing chocolate and cocoa products, sponge cakes, angel food cake, fruit cakes and foam-type cakes and doughnuts.

Optionally, one or more additional enzymes may be used together with the anti-staling amylase of the present invention in preparing dough and dough-based edible products. The additional enzyme may be a starch degrading enzyme, such as, another amylase (e.g., an alpha-amylase, beta-amylase and/or a glucoamylase) or pullulanase, a cyclodextrin glucanotransferase, a peptidase, in particular an exopeptidase, a transglutaminase, a lipase, a phospholipase, a cellulase, a hemicelluase, a protease, a glycosyltransferase, a branching enzyme (1,4-alpha-glucan branching enzyme), an oxidoreductase or oxidase (e.g., a monosaccharide oxidase, such as, glucose oxidase, hexose oxidase, galactose oxidase or pyranose oxidase). Sources of these additional enzymes are well known in the art.

The additional enzyme may be of any origin, including mammalian and plant, and preferably of microbial (bacterial, yeast or fungal) origin. For example, the amylase may be fungal or bacterial, e.g., an alpha-amylase from *Bacillus*, e.g. *B. lichenifornis* or *B. amyloliquefaciens*, a beta-amylase, e.g. from plant (e.g. soy bean) or from microbial sources (e.g. *Bacillus*), a glucoamylase, e.g. from *A. niger*, or a fungal alpha-amylase, e.g. from *A. oryzae*.

The hemicellulase may be a pentosanase, e.g. a xylanase which may be of microbial origin, e.g. derived from a bacterium or fungus, such as a strain of *Aspergillus*, in particular of *A. aculeatus, A. niger, A. awamori*, or *A. tubigensis*, from a strain of *Trichoderma*, e.g. *T. reesei*, or from a strain of *Humicola*, e.g. *H. insolens*.

The protease may be from *Bacillus*, e.g. *B. amyloliquefaciens*.

The lipase may be derived from a strain of *Thermomyces* (*Humicola*), *Rhizomucor, Candida, Aspergillus, Rhizopus*, or *Pseudomonas*, in particular from *T. lanuginosus* (*H. ianuginosa*), *Rhizomucor miehei, C. antarctica, A niger, Rhizopus delemar, Rhizopus arrhizus* or *P. cepacia*.

The phospholipase may have phospholipase A1 or A2 or lysophospholipase activity; it may or may not have lipase activity. It may be of animal origin, e.g. from pancreas, snake venom or bee venom, or it may be of microbial origin, e.g. from filamentous fungi, yeast or bacteria, such as *Aspergillus* or *Fusarium*, e.g. *A. niger, A. oryzae* or *F. oxysporum*. Also the variants described in WO 0032578 may be used.

The oxidoreductase may be a peroxidase, a laccase or a lipoxygenase. The glucose oxidase may be derived from a strain of *Aspergillus* or *Penicillium*, particularly *A. niger, P. notatum, P. amagasakiense* or *P. vitale*. The hexose oxidase may be one described in EP 833563. The pyranose oxidase may be one described in WO 9722257, e.g. derived from *Trametes*, particularly *T. hirsuta*. The galactose oxidase may be one described in WO 0050606.

EXAMPLES

Example 1

Baking Procedure Tegral Allegro Cake

Baking examples on the following Novamyl® variants are included in this example:

TABLE 1

Variants, Mutations, Report number and Study number

| Variant | Substitutions |
|---|---|
| Ref | F188L, D261G, T288P |
| A | Y89F, D261G, T288P, I290V, N375S |
| B | F194Y, D261G, T288P, N375S |
| C | I15T, P191S, D261G, T288P, N375S, S640I |
| D | Y89F, P191S, D261G, T288P |
| E | I15T, Y89F, P191S, D261G, T288P |
| F | Y89F, F194Y, D261G, T288P |
| G | Y89F, D261G, T288P, N375S |
| H | Y89F, P191S, F194Y, D261G, T288P |
| I | Y89F, P191S, D261G, T288P, N375S |
| J | Y89F, P191S, D261G, T288P, Y360N |
| K | Y89F, P191S, D261G, T288P, Y360F |
| L | Y89F, W93Y, P191S, D261G, T288P |
| M | Y89F, W93F, P191S, D261G, T288P |
| N | Y89F, P191S, F194Y, D261G, T288P, N375S |

Recipe
The following recipe was used:

| | % |
|---|---|
| Tegral Allegro mix* | 100 |
| Pasteurized whole egg | 50 |
| Butter | 50 |
| Enzymes | According to trial. In the range 0-25 mg protein enzyme/kg flour. |

*commercially available from Puratos NV/SA, Groot-Bijgaarden, Belgium

Procedure
The ingredients were scaled into a mixing bowl and mixed using an industrial mixer (e.g. Bjørn/Bear AR 5 A Varimixer®) with a suitable paddle speed. 300 g of the dough was poured into forms. The cakes were baked in a suitable oven (e.g. Sveba Dahlin deck oven) for 45 min. at 180° C. The cakes were allowed to cool down at room temperature for 1 hour.

The volumes of the cakes were determined when the cakes had cooled down, using the rape seed displacement method. The cakes were packed under nitrogen in sealed plastic bags and stored at room temperature until analysis.

The cakes were evaluated on day 1, 7 and 14, two cakes were used at each occasion, and three slices of cakes were analyzed from each cake.

The cohesiveness and hardness of the cakes was evaluated using the texture profile analysis (TPA) with TA-XTplus texture analyzer and the water mobility was characterized by low field NMR.

The Texture profile analysis (TPA) was performed as described in Bourne M. C. (2002) 2. ed., Food Texture and Viscosity: Concept and Measurement. Academic Press.

The mobility of free water was determined as described by P. L. Chen, Z. Long, R. Ruan and T. P. Labuza, Nuclear Magnetic Resonance Studies of water Mobility in Bread during Storage. Lebensmittel Wissenschaft and Technologie 30, 178-183 (1997). The mobility of free water has been described in literature to correlate to moistness of bread crumb.

Result
The volume of the cakes can be found in table 2, the volume of cakes without any enzyme is set to 100%.

Compared to cakes with no addition of enzymes the volume of the cakes is not affected by the addition of the reference enzyme (SEQ ID NO.: 1) nor by the addition of variants hereof, i.e. the cakes did not collapse upon addition of enzyme.

TABLE 2

Volume of cakes as a function of added enzyme

| | 0 mg/kg | 5 mg/kg | 10 mg/kg | 25 mg/kg |
|---|---|---|---|---|
| Ref | 100 | | 98 | 97 |
| A | 100 | | 95 | 97 |
| C | 100 | 96 | 96 | |
| E | 100 | 98 | 100 | |

| | 0 mg/kg | 3 mg/kg | 4 mg/kg | 5 mg/kg |
|---|---|---|---|---|
| M | 100 | 94 | 97 | 95 |
| B | 100 | 95 | 94 | 93 |
| D | 100 | 95 | 96 | 96 |

| | 0 mg/kg | 3 mg/kg | 6 mg/kg | 9 mg/kg | 12 mg/kg |
|---|---|---|---|---|---|
| F | 100 | 99 | 99 | 101 | 103 |

| | 0 mg/kg | 2 mg/kg | 4 mg/kg | 6 mg/kg | 8 mg/kg |
|---|---|---|---|---|---|
| D | 100 | 96 | 97 | 94 | |
| H | 100 | 97 | 93 | 94 | |
| N | 100 | 95 | 95 | 95 | |
| J | 100 | 93 | 93 | 92 | |
| K | 100 | 94 | 92 | 90 | |
| I | 100 | 94 | 97 | 96 | |
| L | 100 | 99 | 98 | 97 | |
| G | 100 | | 93 | 92 | 94 |

The cohesiveness of the cakes decreased with storage time. The addition of variants of Novamyl® delayed this decrease as can be seen in Table 3.

TABLE 3

Change in Cohesiveness of cakes with time measured with the TPA method

| | Dosage | Day 1 | Day 7 | Day 14 |
|---|---|---|---|---|
| No enzyme | — | 0.46 | 0.36 | 0.32 |
| Ref | 10 mg/kg | 0.45 | 0.42 | 0.39 |
| | 25 mg/kg | 0.45 | 0.42 | 0.42 |

TABLE 3-continued

Change in Cohesiveness of cakes with time measured with the TPA method

|   | Dosage | Day 1 | Day 7 | Day 15 |
|---|---|---|---|---|
| A | 10 mg/kg | 0.44 | 0.40 | 0.38 |
|   | 25 mg/kg | 0.43 | 0.42 | 0.40 |
| No enzyme | — | 0.52 | 0.43 | 0.39 |
| Ref | 10 mg/kg | 0.56 | 0.49 | 0.44 |
|   | 25 mg/kg | 0.57 | 0.52 | 0.49 |
| H | 2 mg/kg | 0.56 | 0.49 | 0.45 |
|   | 4 mg/kg | 0.58 | 0.51 | 0.48 |
|   | 6 mg/kg | 0.56 | 0.51 | 0.48 |
| N | 2 mg/kg | 0.54 | 0.47 | 0.45 |
|   | 4 mg/kg | 0.57 | 0.53 | 0.47 |
|   | 6 mg/kg | 0.56 | 0.52 | 0.48 |
| D | 2 mg/kg | 0.57 | 0.48 | 0.45 |
|   | 4 mg/kg | 0.55 | 0.50 | 0.46 |
|   | 6 mg/kg | 0.55 | 0.49 | 0.46 |

|   | Dosage | Day 1 | Day 7 | Day 15 |
|---|---|---|---|---|
| No enzyme | — | 0.52 | 0.42 | 0.36 |
| Ref | 10 mg/kg | 0.54 | 0.48 | 0.44 |
|   | 25 mg/kg | 0.56 | 0.50 | 0.46 |
| J | 2 mg/kg | 0.54 | 0.46 | 0.41 |
|   | 4 mg/kg | 0.53 | 0.47 | 0.42 |
|   | 6 mg/kg | 0.54 | 0.49 | 0.44 |
| K | 2 mg/kg | 0.54 | 0.46 | 0.40 |
|   | 4 mg/kg | 0.53 | 0.48 | 0.43 |
|   | 6 mg/kg | 0.53 | 0.48 | 0.43 |

|   | Dosage | Day 1 | Day 7 | Day 14 |
|---|---|---|---|---|
| No enzyme | — | 0.50 | 0.47 | 0.43 |
| Ref | 10 mg/kg | 0.54 | 0.51 | 0.48 |
|   | 25 mg/kg | 0.55 | 0.55 | 0.52 |
| I | 2 mg/kg | 0.53 | 0.51 | 0.48 |
|   | 4 mg/kg | 0.54 | 0.53 | 0.50 |
|   | 6 mg/kg | 0.51 | 0.50 | 0.49 |
| L | 2 mg/kg | 0.52 | 0.49 | 0.47 |
|   | 4 mg/kg | 0.54 | 0.51 | 0.49 |
|   | 6 mg/kg | 0.53 | 0.52 | 0.51 |

|   | Dosage | Day 1 | Day 6 | Day 14 |
|---|---|---|---|---|
| No enzyme | — | 0.46 | 0.38 | 0.35 |
| Ref | 10 mg/kg | 0.49 | 0.43 | 0.42 |
|   | 25 mg/kg | 0.48 | 0.44 | 0.44 |
| E | 5 mg/kg | 0.47 | 0.42 | 0.39 |
|   | 10 mg/kg | 0.47 | 0.41 | 0.41 |

|   | Dosage | Day 1 | Day 7 | Day 14 |
|---|---|---|---|---|
| No enzyme | — | 0.43 | 0.33 | 0.28 |
| Ref | 10 mg/kg | 0.45 | 0.38 | 0.35 |
|   | 25 mg/kg | 0.45 | 0.40 | 0.37 |
| G | 4 mg/kg | 0.46 | 0.36 | 0.34 |
|   | 6 mg/kg | 0.45 | 0.40 | 0.37 |
|   | 8 mg/kg | 0.44 | 0.38 | 0.37 |

|   | Dosage | Day 3 | Day 7 | Day 14 |
|---|---|---|---|---|
| No enzyme | — | 0.45 | 0.41 | 0.37 |
| Ref | 10 mg/kg | 0.50 | 0.47 | 0.45 |
|   | 25 mg/kg | 0.51 | 0.49 | 0.48 |
| D | 3 mg/kg | 0.48 | 0.46 | 0.43 |
|   | 4 mg/kg | 0.50 | 0.48 | 0.45 |
|   | 5 mg/kg | 0.50 | 0.47 | 0.45 |
| B | 3 mg/kg | 0.50 | 0.48 | 0.45 |
|   | 4 mg/kg | 0.51 | 0.49 | 0.47 |
|   | 5 mg/kg | 0.52 | 0.49 | 0.47 |
| M | 3 mg/kg | 0.50 | 0.48 | 0.45 |
|   | 4 mg/kg | 0.50 | 0.47 | 0.45 |
|   | 5 mg/kg | 0.51 | 0.49 | 0.46 |

|   | Dosage | Day 1 | Day 7 | Day 14 |
|---|---|---|---|---|
| No enzyme | — | 0.42 | 0.34 | 0.31 |
| Ref | 10 mg/kg | 0.44 | 0.40 | 0.38 |
|   | 25 mg/kg | 0.44 | 0.43 | 0.40 |
| F | 3 mg/kg | 0.43 | 0.39 | 0.34 |
|   | 6 mg/kg | 0.43 | 0.40 | 0.35 |
|   | 9 mg/kg | 0.43 | 0.40 | 0.35 |
|   | 12 mg/kg | 0.43 | 0.43 | 0.36 |
| No enzyme | — | 0.40 | 0.32 | 0.28 |
| Ref | 10 mg/kg | 0.42 | 0.38 | 0.35 |
|   | 25 mg/kg | 0.44 | 0.40 | 0.40 |
| C | 5 mg/kg | 0.43 | 0.36 | 0.33 |
|   | 10 mg/kg | 0.42 | 0.36 | 0.34 |

The hardness of the cakes increased with storage time. The addition of variants of Novamyl® delayed this increase in hardness as can be seen in Table 4.

TABLE 4

Change in Hardness [g] of cakes with time measured with the TPA method

|   | Dosage | Day 1 | Day 7 | Day 14 |
|---|---|---|---|---|
| No enzyme | — | 586 | 875 | 1093 |
| Ref | 10 mg/kg | 597 | 768 | 955 |
|   | 25 mg/kg | 603 | 732 | 957 |
| A | 10 mg/kg | 612 | 801 | 953 |
|   | 25 mg/kg | 602 | 731 | 827 |
| No enzyme | — | 515 | 811 | 1046 |
| Ref | 10 mg/kg | 438 | 651 | 762 |
|   | 25 mg/kg | 530 | 687 | 869 |
| H | 2 mg/kg | 521 | 809 | 892 |
|   | 4 mg/kg | 573 | 773 | 908 |
|   | 6 mg/kg | 523 | 702 | 797 |
| N | 2 mg/kg | 516 | 751 | 898 |
|   | 4 mg/kg | 484 | 668 | 872 |
|   | 6 mg/kg | 565 | 753 | 821 |
| D | 2 mg/kg | 556 | 794 | 1015 |
|   | 4 mg/kg | 524 | 715 | 953 |
|   | 6 mg/kg | 521 | 716 | 876 |

|   | Dosage | Day 1 | Day 7 | Day 15 |
|---|---|---|---|---|
| No enzyme | — | 484 | 738 | 956 |
| Ref | 10 mg/kg | 518 | 753 | 976 |
|   | 25 mg/kg | 559 | 714 | 868 |
| J | 2 mg/kg | 576 | 823 | 1058 |
|   | 4 mg/kg | 549 | 761 | 908 |
|   | 6 mg/kg | 601 | 798 | 1092 |
| K | 2 mg/kg | 584 | 889 | 1081 |
|   | 4 mg/kg | 551 | 811 | 993 |
|   | 6 mg/kg | 564 | 782 | 935 |

|   | Dosage | Day 1 | Day 7 | Day 14 |
|---|---|---|---|---|
| No enzyme | — | 760 | 1064 | 1397 |
| Ref | 10 mg/kg | 748 | 943 | 1175 |
|   | 25 mg/kg | 747 | 937 | 1101 |
| I | 2 mg/kg | 821 | 1085 | 1394 |
|   | 4 mg/kg | 829 | 1089 | 1315 |
|   | 6 mg/kg | 756 | 947 | 1071 |
| L | 2 mg/kg | 795 | 1033 | 1363 |
|   | 4 mg/kg | 808 | 1062 | 1164 |
|   | 6 mg/kg | 770 | 1020 | 1160 |

TABLE 4-continued

Change in Hardness [g] of cakes with time measured with the TPA method

| | Dosage | Day 1 | Day 6 | Day 14 |
|---|---|---|---|---|
| No enzyme | — | 602 | 984 | 1172 |
| Ref | 10 mg/kg | 636 | 897 | 1035 |
| | 25 mg/kg | 627 | 851 | 1018 |
| E | 5 mg/kg | 660 | 987 | 1176 |
| | 10 mg/kg | 644 | 894 | 1023 |

| | Dosage | Day 1 | Day 7 | Day 14 |
|---|---|---|---|---|
| No enzyme | — | 480 | 966 | 1284 |
| Ref | 10 mg/kg | 593 | 961 | 1106 |
| | 25 mg/kg | 535 | 843 | 1079 |
| G | 4 mg/kg | 692 | 985 | 1336 |
| | 6 mg/kg | 637 | 1095 | 1287 |
| | 8 mg/kg | 616 | 1074 | 1214 |

| | Dosage | Day 3 | Day 7 | Day 14 |
|---|---|---|---|---|
| No enzyme | — | 595 | 827 | 981 |
| Ref | 10 mg/kg | 641 | 829 | 1020 |
| | 25 mg/kg | 589 | 657 | 809 |
| D | 3 mg/kg | 599 | 766 | 987 |
| | 4 mg/kg | 678 | 801 | 1009 |
| | 5 mg/kg | 652 | 847 | 1018 |
| B | 3 mg/kg | 627 | 767 | 973 |
| | 4 mg/kg | 639 | 780 | 923 |
| | 5 mg/kg | 578 | 768 | 960 |
| M | 3 mg/kg | 679 | 772 | 1014 |
| | 4 mg/kg | 601 | 814 | 1005 |
| | 5 mg/kg | 646 | 789 | 957 |

| | Dosage | Day 1 | Day 7 | Day 14 |
|---|---|---|---|---|
| No enzyme | — | 616 | 1038 | 1255 |
| Ref | 10 mg/kg | 682 | 912 | 1155 |
| | 25 mg/kg | 640 | 844 | 1077 |
| F | 3 mg/kg | 683 | 843 | 1131 |
| | 6 mg/kg | 626 | 831 | 1131 |
| | 9 mg/kg | 644 | 785 | 947 |
| | 12 mg/kg | 571 | 903 | 992 |
| No enzyme | — | 469 | 724 | 952 |
| Ref | 10 mg/kg | 474 | 672 | 956 |
| | 25 mg/kg | 515 | 661 | 873 |
| C | 5 mg/kg | 546 | 800 | 1050 |
| | 10 mg/kg | 546 | 753 | 993 |

The free water mobility is correlated with the moist perception of the cake crumb, it decreases with time. The addition of the Novamyl® variants increased the mobility compared to the control, indicating that the amylases were able to keep the cakes more moist. Results are listed in Table 5.

TABLE 5

Change in Free water mobility [μs] of cakes with time measured with low field NMR

| | Dosage | Day 1 | Day 7 | Day 14 |
|---|---|---|---|---|
| No enzyme | — | 7703 | 5339 | 4138 |
| Ref | 10 mg/kg | 7755 | 5670 | 4434 |
| | 25 mg/kg | 7502 | 5751 | 4366 |
| A | 10 mg/kg | 7809 | 6124 | 4839 |
| | 25 mg/kg | 7753 | 6175 | 4811 |
| No enzyme | — | 6464 | 5577 | 4618 |
| Ref | 10 mg/kg | 7009 | 5507 | 4831 |
| | 25 mg/kg | 7109 | 5897 | 5004 |
| H | 2 mg/kg | 6819 | 5521 | 4743 |
| | 4 mg/kg | 7171 | 5906 | 5157 |
| | 6 mg/kg | 7340 | 6196 | 5131 |
| N | 2 mg/kg | 7034 | 5697 | 4955 |
| | 4 mg/kg | 6897 | 6024 | 5067 |
| | 6 mg/kg | 7196 | 6184 | 5368 |
| D | 2 mg/kg | 6936 | 5753 | 4910 |
| | 4 mg/kg | 7169 | 5787 | 5031 |
| | 6 mg/kg | 6876 | 5983 | 5228 |

| | Dosage | Day 1 | Day 7 | Day 15 |
|---|---|---|---|---|
| No enzyme | — | 7358 | 5537 | 4385 |
| Ref | 10 mg/kg | 7606 | 5735 | 4830 |
| | 25 mg/kg | 7456 | 5648 | 4977 |
| J | 2 mg/kg | 7502 | 5638 | 4818 |
| | 4 mg/kg | 7575 | 5663 | 5081 |
| | 6 mg/kg | 7853 | 6093 | 5193 |
| K | 2 mg/kg | 7714 | 5649 | 4845 |
| | 4 mg/kg | 7999 | 5766 | 5022 |
| | 6 mg/kg | 8029 | 6291 | 5312 |

| | Dosage | Day 1 | Day 7 | Day 14 |
|---|---|---|---|---|
| No enzyme | — | 7004 | 4887 | 4266 |
| Ref | 10 mg/kg | 7354 | 5331 | 4567 |
| | 25 mg/kg | 7489 | 5486 | 4856 |
| I | 2 mg/kg | 7569 | 5374 | 4766 |
| | 4 mg/kg | 7596 | 5241 | 4925 |
| | 6 mg/kg | 7710 | 5673 | 5110 |
| L | 2 mg/kg | 7495 | 5101 | 4647 |
| | 4 mg/kg | 7433 | 5228 | 4821 |
| | 6 mg/kg | 7577 | 5342 | 4988 |

| | Dosage | Day 1 | Day 6 | Day 14 |
|---|---|---|---|---|
| No enzyme | — | 7137 | 5308 | 4130 |
| Ref | 10 mg/kg | 7523 | 6554 | 4751 |
| | 25 mg/kg | 7449 | 5808 | 4778 |
| E | 5 mg/kg | 7387 | 6227 | 4725 |
| | 10 mg/kg | 7288 | 5670 | 4786 |

| | Dosage | Day 1 | Day 7 | Day 14 |
|---|---|---|---|---|
| No enzyme | — | 6954 | 5037 | 4152 |
| Ref | 10 mg/kg | 7307 | 5384 | 4278 |
| | 25 mg/kg | 7461 | 5323 | 4440 |
| G | 4 mg/kg | 7240 | 5254 | 4435 |
| | 6 mg/kg | 7077 | 5371 | 4659 |
| | 8 mg/kg | 7207 | 5634 | 4893 |

| | Dosage | Day 3 | Day 7 | Day 14 |
|---|---|---|---|---|
| No enzyme | — | 6322 | 5101 | 4458 |
| Ref | 10 mg/kg | 6037 | 5452 | 4769 |
| | 25 mg/kg | 6882 | 5515 | 5304 |
| D | 3 mg/kg | 6604 | 5446 | 4952 |
| | 4 mg/kg | 6373 | 5466 | 4550 |
| | 5 mg/kg | 6460 | 5507 | 4891 |
| B | 3 mg/kg | 7126 | 5896 | 5334 |
| | 4 mg/kg | 7134 | 5774 | 5341 |
| | 5 mg/kg | 7117 | 6014 | 5203 |
| M | 3 mg/kg | 7054 | 5917 | 5189 |
| | 4 mg/kg | 6449 | 5362 | 4833 |
| | 5 mg/kg | 7057 | 5501 | 5173 |

| | Dosage | Day 1 | Day 7 | Day 14 |
|---|---|---|---|---|
| No enzyme | — | 7285 | 4791 | 3766 |
| Ref | 10 mg/kg | 7410 | 5437 | 4542 |
| | 25 mg/kg | 7367 | 4959 | 4511 |
| F | 3 mg/kg | 7114 | 5462 | 4593 |
| | 6 mg/kg | 7457 | 5698 | 4648 |
| | 9 mg/kg | 7298 | 5309 | 4293 |
| | 12 mg/kg | 7528 | 5938 | 4599 |

TABLE 5-continued

Change in Free water mobility [μs] of cakes with time measured with low field NMR

| | Dosage | | | |
|---|---|---|---|---|
| No enzyme | — | 6722 | 4344 | 3477 |
| Ref | 10 mg/kg | 6816 | 4761 | 3769 |
| | 25 mg/kg | 7008 | 5109 | 3923 |
| C | 5 mg/kg | 6606 | 5623 | 4265 |
| | 10 mg/kg | 6746 | 4782 | 3690 |

The invention claimed is:
1. A method of preparing a dough or a dough-based edible product, comprising adding a polypeptide to the dough, wherein the dough comprises at least 10% sucrose by weight, and the polypeptide:
- has an amino acid sequence which is at least 70% identical to SEQ ID NO: 1, and
- compared to SEQ ID NO: 1 comprises the two substitutions D261G and T288P and at least one additional amino acid alteration which is substitution or deletion of or insertion adjacent to Y89, W93, P191, F194, Y360, or N375.

2. The method of claim 1, wherein the at least one additional amino acid alteration comprises at least two amino acid alterations.

3. The method of claim 1, wherein the at least one additional amino acid alteration comprises at least four amino acid alterations.

4. The method of claim 1, wherein the at least one additional amino acid alteration comprises at least six amino acid alterations.

5. The method of claim 1, wherein the at least one additional amino acid alteration comprises a combination of two or more amino acid alterations in positions compared to SEQ ID NO: 1, selected from the group of position combinations consisting of:
Y89+W93
Y89+P191
Y89+F194
Y89+Y360
Y89+N375
W93+P191
W93+F194
W93+Y360
W93+N375
P191+F194
P191+Y360
P191+N375
F194+Y360
F194+N375
Y360+N375
Y89+W93+P191
Y89+W93+F194
Y89+W93+Y360
Y89+W93+N375
Y89+P191+F194
Y89+P191+Y360
Y89+P191+N375
Y89+F194+Y360
Y89+F194+N375
Y89+Y360+N375
W93+P191+F194
W93+P191+Y360
W93+P191+N375
W93+F194+Y360
W93+F194+N375
W93+Y360+N375
P191+F194+Y360
P191+F194+N375
P191+Y360+N375
F194+Y360+N375
Y89+W93+P191+F194
Y89+W93+P191+Y360
Y89+W93+P191+N375
Y89+W93+F194+Y360
Y89+W93+F194+N375
Y89+W93+Y360+N375
Y89+P191+F194+Y360
Y89+P191+F194+N375
Y89+P191+Y360+N375
Y89+F194+Y360+N375
W93+P191+F194+Y360
W93+P191+F194+N375
W93+P191+Y360+N375
W93+F194+Y360+N375
P191+F194+Y360+N375
Y89+W93+P191+F194+Y360
Y89+W93+P191+F194+N375
Y89+W93+P191+Y360+N375
Y89+W93+F194+Y360+N375
Y89+P191+F194+Y360+N375
W93+P191+F194+Y360+N375
Y89+W93+P191+F194+Y360+N375.

6. The method of claim 1, wherein the at least one amino acid alteration comprises one or more of the following substitutions, alone or in combination:
Y89F,W
W93F,Y
P191S,N
F194Y,S,L
Y360F,I,N
N375S,T.

7. The method of claim 1, wherein the amino acid alteration is substitution with a larger or smaller amino acid residue.

8. The method of claim 1, wherein the alteration is insertion of 1-4 amino acid residues at the N- or C-side of the specified residue.

9. The method of claim 1, wherein the polypeptide comprises a substitution I15T/S/V/L, R18K, K44R/S/T/Q/N, N86Q/S/T, T87N/Q/S, G88A/S/T, Y89W/F/H, H90W/F/Y/R/K/N/Q/M, W93Y/F/M/E/G/V/T/S, F188H/L/I/T/G/V, D190E/Q/G, A192G/S/T/Q/R, F194S/L/Y, L196F, N371K/R/F/Y/Q or D372E/Q/S/T/A, a deletion of 191 or 192 or an insertion of Ala after 192.

10. The method of claim 1, wherein the polypeptide has the amino acid sequence of SEQ ID NO: 1 with one of the following combinations of amino acid alterations:
Y89F, D261G, T288P, I290V, N375S
F194Y, D261G, T288P, N375S
I15T, P191S, D261G, T288P, N375S, S6401
Y89F, P191S, D261G, T288P
I15T, Y89F, P191S, D261G, T288P
Y89F, F194Y, D261G, T288P
Y89F, D261G, T288P, N375S
Y89F, P191S, F194Y, D261G, T288P
Y89F, P191S, D261G, T288P, N3755
Y89F, P191S, D261G, T288P, Y360N
Y89F, P191S, D261G, T288P, Y360F
Y89F, W93Y, P191S, D261G, T288P
Y89F, W93F, P191S, D261G, T288P
Y89F, P191S, F194Y, D261G, T288P, N375S.

11. An isolated polypeptide which:
- has amylase activity which is less inhibited by sucrose than the amylase activity of SEQ ID NO: 1,
- has an amino acid sequence which is at least 70% identical to SEQ ID NO: 1, and
- compared to SEQ ID NO: 1 comprises the two substitutions D261G and T288P and at least one additional amino acid alteration which is substitution or deletion of or insertion adjacent to Y89, W93, P191, F194, Y360, or N375.

12. The polypeptide of claim 11, wherein the at least one additional amino acid alteration comprises at least two amino acid alterations.

13. The polypeptide of claim 11, wherein the at least one additional amino acid alteration comprises at least four amino acid alterations.

14. The polypeptide of claim 11, wherein the at least one additional amino acid alteration comprises at least six amino acid alterations.

15. The polypeptide of claim 11, wherein the at least one additional amino acid alteration comprises a combination of two or more amino acid alterations in positions compared to SEQ ID NO: 1, selected from the group of position combinations consisting of:

Y89+W93
Y89+P191
Y89+F194
Y89+Y360
Y89+N375
W93+P191
W93+F194
W93+Y360
W93+N375
P191+F194
P191+Y360
P191+N375
F194+Y360
F194+N375
Y360+N375
Y89+W93+P191
Y89+W93+F194
Y89+W93+Y360
Y89+W93+N375
Y89+P191+F194
Y89+P191+Y360
Y89+P191+N375
Y89+F194+Y360
Y89+F194+N375
Y89+Y360+N375
W93+P191+F194
W93+P191+Y360
W93+P191+N375
W93+F194+Y360
W93+F194+N375
W93+Y360+N375
P191+F194+Y360
P191+F194+N375
P191+Y360+N375
F194+Y360+N375
Y89+W93+P191+F194
Y89+W93+P191+Y360
Y89+W93+P191+N375
Y89+W93+F194+Y360
Y89+W93+F194+N375
Y89+W93+Y360+N375
Y89+P191+F194+Y360
Y89+P191+F194+N375
Y89+P191+Y360+N375
Y89+F194+Y360+N375
W93+P191+F194+Y360
W93+P191+F194+N375
W93+P191+Y360+N375
W93+F194+Y360+N375
P191+F194+Y360+N375
Y89+W93+P191+F194+Y360
Y89+W93+P191+F194+N375
Y89+W93+P191+Y360+N375
Y89+W93+F194+Y360+N375
Y89+P191+F194+Y360+N375
W93+P191+F194+Y360+N375
Y89+W93+P191+F194+Y360+N375.

16. The polypeptide of claim 11, wherein the at least one amino acid alteration comprises one or more of the following substitutions, alone or in combination:

Y89F,W
W93F,Y
P191S,N
F194Y,S,L
Y360F,I,N
N375S,T.

17. The polypeptide of claim 11, wherein the alteration is substitution with a larger or smaller amino acid residue.

18. The polypeptide of claim 11, which comprises insertion of 1-4 amino acid residues at the N- or C-side of the specified residue.

19. The polypeptide of claim 11, which has the amino acid sequence of SEQ ID NO: 1 with one of the following combinations of amino acid alterations Y89F, D261G, T288P, I290V, N375S
F194Y, D261G, T288P, N375S
I15T, P191S, D261G, T288P, N375S, S640I
Y89F, P191S, D261G, T288P
I15T, Y89F, P191S, D261G, T288P
Y89F, F194Y, D261G, T288P
Y89F, D261G, T288P, N375S
Y89F, P191S, F194Y, D261G, T288P
Y89F, P191S, D261G, T288P, N375S
Y89F, P191S, D261G, T288P, Y360N
Y89F, P191S, D261G, T288P, Y360F
Y89F, W93Y, P191S, D261G, T288P
Y89F, W93F, P191S, D261G, T288P
Y89F, P191S, F194Y, D261G, T288P, N375S.

20. A method of preparing a polypeptide, comprising
providing a parent polypeptide having an amino acid sequence and having maltogenic alpha-amylase activity,
selecting at least one amino acid residue in the sequence corresponding to Y360 in SEQ ID NO: 1 or selecting a combination of two or more amino acid residues in positions corresponding to SEQ ID NO: 1, selected from the group of combinations consisting of:

Y89+W93
Y89+P191
Y89+F194
Y89+Y360
Y89+N375
W93+P191
W93+F194
W93+Y360
W93+N375
P191+F194
P191+Y360
P191+N375
F194+Y360
F194+N375
Y360+N375
Y89+W93+P191
Y89+W93+F194
Y89+W93+Y360
Y89+W93+N375
Y89+P191+F194
Y89+P191+Y360
Y89+P191+N375
Y89+F194+Y360
Y89+F194+N375
Y89+Y360+N375
W93+P191+F194
W93+P191+Y360

W93+P191+N375
W93+F194+Y360
W93+F194+N375
W93+Y360+N375
P191+F194+Y360
P191+F194+N375
P191+Y360+N375
F194+Y360+N375
Y89+W93+P191+F194
Y89+W93+P191+Y360
Y89+W93+P191+N375
Y89+W93+F194+Y360
Y89+W93+F194+N375
Y89+W93+Y360+N375
Y89+P191+F194+Y360
Y89+P191+F194+N375
Y89+P191+Y360+N375
Y89+F194+Y360+N375
W93+P191+F194+Y360
W93+P191+F194+N375
W93+P191+Y360+N375
W93+F194+Y360+N375
P191+F194+Y360+N375
Y89+W93+P191+F194+Y360
Y89+W93+P191+F194+N375
Y89+W93+P191+Y360+N375
Y89+W93+F194+Y360+N375
Y89+P191+F194+Y360+N375
W93+P191+F194+Y360+N375
Y89+W93+P191+F194+Y360+N375 substituting or deleting the selected residue(s) or inserting one or more residues adjacent to the selected residue(s) to obtain an altered amino acid sequence, preparing an altered polypeptide having the altered amino acid sequence, testing the amylase activity and the sugar tolerance of the altered polypeptide, and selecting a polypeptide which has amylase activity and has higher sucrose tolerance than the parent polypeptide.

* * * * *

SEQUENCE LISTING

<160> NUMBER OF SEQ ID NOS: 1

<210> SEQ ID NO 1
<211> LENGTH: 686
<212> TYPE: PRT
<213> ORGANISM: Bacillus stearothermophilus

<400> SEQUENCE: 1

```
Ser Ser Ser Ala Ser Val Lys Gly Asp Val Ile Tyr Gln Ile Ile Ile
1               5                   10                  15

Asp Arg Phe Tyr Asp Gly Asp Thr Thr Asn Asn Asn Pro Ala Lys Ser
            20                  25                  30

Tyr Gly Leu Tyr Asp Pro Thr Lys Ser Lys Trp Lys Met Tyr Trp Gly
        35                  40                  45

Gly Asp Leu Glu Gly Val Arg Gln Lys Leu Pro Tyr Leu Lys Gln Leu
    50                  55                  60

Gly Val Thr Thr Ile Trp Leu Ser Pro Val Leu Asp Asn Leu Asp Thr
65                  70                  75                  80

Leu Ala Gly Thr Asp Asn Thr Gly Tyr His Gly Tyr Trp Thr Arg Asp
                85                  90                  95

Phe Lys Gln Ile Glu Glu His Phe Gly Asn Trp Thr Thr Phe Asp Thr
            100                 105                 110

Leu Val Asn Asp Ala His Gln Asn Gly Ile Lys Val Ile Val Asp Phe
        115                 120                 125

Val Pro Asn His Ser Thr Pro Phe Lys Ala Asn Asp Ser Thr Phe Ala
    130                 135                 140

Glu Gly Gly Ala Leu Tyr Asn Asn Gly Thr Tyr Met Gly Asn Tyr Phe
145                 150                 155                 160

Asp Asp Ala Thr Lys Gly Tyr Phe His His Asn Gly Asp Ile Ser Asn
                165                 170                 175

Trp Asp Asp Arg Tyr Glu Ala Gln Trp Lys Asn Phe Thr Asp Pro Ala
            180                 185                 190

Gly Phe Ser Leu Ala Asp Leu Ser Gln Glu Asn Gly Thr Ile Ala Gln
        195                 200                 205

Tyr Leu Thr Asp Ala Ala Val Gln Leu Val Ala His Gly Ala Asp Gly
    210                 215                 220

Leu Arg Ile Asp Ala Val Lys His Phe Asn Ser Gly Phe Ser Lys Ser
225                 230                 235                 240

Leu Ala Asp Lys Leu Tyr Gln Lys Lys Asp Ile Phe Leu Val Gly Glu
                245                 250                 255

Trp Tyr Gly Asp Asp Pro Gly Thr Ala Asn His Leu Glu Lys Val Arg
            260                 265                 270

Tyr Ala Asn Asn Ser Gly Val Asn Val Leu Asp Phe Asp Leu Asn Thr
        275                 280                 285

Val Ile Arg Asn Val Phe Gly Thr Phe Thr Gln Thr Met Tyr Asp Leu
```

```
            290                 295                 300
Asn Asn Met Val Asn Gln Thr Gly Asn Glu Tyr Lys Tyr Lys Glu Asn
305                 310                 315                 320

Leu Ile Thr Phe Ile Asp Asn His Asp Met Ser Arg Phe Leu Ser Val
                325                 330                 335

Asn Ser Asn Lys Ala Asn Leu His Gln Ala Leu Ala Phe Ile Leu Thr
            340                 345                 350

Ser Arg Gly Thr Pro Ser Ile Tyr Tyr Gly Thr Glu Gln Tyr Met Ala
        355                 360                 365

Gly Gly Asn Asp Pro Tyr Asn Arg Gly Met Met Pro Ala Phe Asp Thr
370                 375                 380

Thr Thr Thr Ala Phe Lys Glu Val Ser Thr Leu Ala Gly Leu Arg Arg
385                 390                 395                 400

Asn Asn Ala Ala Ile Gln Tyr Gly Thr Thr Gln Arg Trp Ile Asn
                405                 410                 415

Asn Asp Val Tyr Ile Tyr Glu Arg Lys Phe Phe Asn Asp Val Val Leu
            420                 425                 430

Val Ala Ile Asn Arg Asn Thr Gln Ser Ser Tyr Ser Ile Ser Gly Leu
        435                 440                 445

Gln Thr Ala Leu Pro Asn Gly Ser Tyr Ala Asp Tyr Leu Ser Gly Leu
450                 455                 460

Leu Gly Gly Asn Gly Ile Ser Val Ser Asn Gly Ser Val Ala Ser Phe
465                 470                 475                 480

Thr Leu Ala Pro Gly Ala Val Ser Val Trp Gln Tyr Ser Thr Ser Ala
                485                 490                 495

Ser Ala Pro Gln Ile Gly Ser Val Ala Pro Asn Met Gly Ile Pro Gly
            500                 505                 510

Asn Val Val Thr Ile Asp Gly Lys Gly Phe Gly Thr Thr Gln Gly Thr
        515                 520                 525

Val Thr Phe Gly Gly Val Thr Ala Thr Val Lys Ser Trp Thr Ser Asn
530                 535                 540

Arg Ile Glu Val Tyr Val Pro Asn Met Ala Ala Gly Leu Thr Asp Val
545                 550                 555                 560

Lys Val Thr Ala Gly Gly Val Ser Ser Asn Leu Tyr Ser Tyr Asn Ile
                565                 570                 575

Leu Ser Gly Thr Gln Thr Ser Val Val Phe Thr Val Lys Ser Ala Pro
            580                 585                 590

Pro Thr Asn Leu Gly Asp Lys Ile Tyr Leu Thr Gly Asn Ile Pro Glu
        595                 600                 605

Leu Gly Asn Trp Ser Thr Asp Thr Ser Gly Ala Val Asn Asn Ala Gln
610                 615                 620

Gly Pro Leu Leu Ala Pro Asn Tyr Pro Asp Trp Phe Tyr Val Phe Ser
625                 630                 635                 640

Val Pro Ala Gly Lys Thr Ile Gln Phe Lys Phe Ile Lys Arg Ala
                645                 650                 655

Asp Gly Thr Ile Gln Trp Glu Asn Gly Ser Asn His Val Ala Thr Thr
            660                 665                 670

Pro Thr Gly Ala Thr Gly Asn Ile Thr Val Thr Trp Gln Asn
        675                 680                 685
```